US010772735B2

(12) United States Patent
Kakar et al.

(10) Patent No.: US 10,772,735 B2
(45) Date of Patent: Sep. 15, 2020

(54) DISTAL RADIOULNAR JOINT PROSTHESIS AND METHOD OF USE

(71) Applicant: MAYO FOUNDATION FOR MEDICAL EDUCATION AND RESEARCH, Rochester, MN (US)

(72) Inventors: Sanjeev Kakar, Rochester, MN (US); Aaron C. Babb, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 109 days.

(21) Appl. No.: 15/570,487

(22) PCT Filed: Apr. 29, 2016

(86) PCT No.: PCT/US2016/029947
§ 371 (c)(1),
(2) Date: Oct. 30, 2017

(87) PCT Pub. No.: WO2016/178946
PCT Pub. Date: Nov. 10, 2016

(65) Prior Publication Data
US 2018/0140429 A1    May 24, 2018

Related U.S. Application Data

(60) Provisional application No. 62/155,518, filed on May 1, 2015.

(51) Int. Cl.
*A61F 2/42* (2006.01)
*A61F 2/30* (2006.01)

(52) U.S. Cl.
CPC .... *A61F 2/4261* (2013.01); *A61F 2002/3055* (2013.01); *A61F 2002/30331* (2013.01);
(Continued)

(58) Field of Classification Search
CPC ................ A61F 2/4261; A61F 2002/4269
See application file for complete search history.

(56) References Cited

U.S. PATENT DOCUMENTS 3,579,830 A    5/1971  Morel
4,693,723 A    9/1987  Gabard
(Continued)

FOREIGN PATENT DOCUMENTS

FR    2660856 A1 * 10/1991 ........... A61F 2/4261

OTHER PUBLICATIONS

PCT International Search Report and Written Opinion, PCT/US2016/029947, dated Jul. 28, 2016, 16 pages.

*Primary Examiner* — David H Willse
*Assistant Examiner* — Javier G Blanco
(74) *Attorney, Agent, or Firm* — Quarles & Brady LLP (57) ABSTRACT

A distal radioulnar joint prosthesis for replacing the distal radioulnar joint and a method for its implantation is provided. Such a device includes an ulnar component, a radial component, and a motion liner. The ulnar component includes a stem, a collar, and a shell. The radial component includes a hemispherical ball and plate. The hemispherical ball of the radial component is secured with the radial plate and articulates with the ulnar shell via the motion liner. The prosthesis is designed to more accurately replicate the biomechanics of the distal wrist than currently used implants.

22 Claims, 7 Drawing Sheets

(52) U.S. Cl.
CPC .............. *A61F 2002/30433* (2013.01); *A61F 2002/30616* (2013.01); *A61F 2002/30649* (2013.01); *A61F 2002/4269* (2013.01)

(56) References Cited

U.S. PATENT DOCUMENTS

| | | | |
|---|---|---|---|
| 5,108,444 A | | 4/1992 | Branemark |
| 5,133,762 A | * | 7/1992 | Branemark ........... A61F 2/4261 623/21.12 |
| 5,462,563 A | | 10/1995 | Shearer et al. |
| 5,507,824 A | | 4/1996 | Lennox |
| 7,875,082 B2 | | 1/2011 | Naidu |
| 8,048,162 B2 | | 11/2011 | Scheker et al. |
| 8,088,168 B2 | | 1/2012 | Hassler et al. |
| 8,852,285 B2 | | 10/2014 | Greenberg |
| 2006/0161260 A1 | | 7/2006 | Thomas et al. |
| 2009/0043342 A1 | * | 2/2009 | Freedland .......... A61B 17/0401 606/313 |
| 2009/0254189 A1 | | 10/2009 | Scheker |
| 2010/0312354 A1 | * | 12/2010 | Bandoh ............... A61F 2/30942 623/23.15 |
| 2012/0191199 A1 | | 7/2012 | Raemisch |
| 2013/0245778 A1 | * | 9/2013 | Greenberg ........... A61F 2/4261 623/21.12 |
| 2013/0338780 A1 | | 12/2013 | Berchoux et al. |

\* cited by examiner

Fig. 9 ns
DISTAL RADIOULNAR JOINT PROSTHESIS AND METHOD OF USE

CROSS-REFERENCE TO RELATED APPLICATIONS

This application represents the national stage entry of PCT International Application No. PCT/US2016/029947 filed on Apr. 29, 2016 and claims priority to U.S. Provisional Patent Application Ser. No. 62/155,518 filed May 1, 2015, the contents of which are hereby incorporated by reference as if set forth in their entirety herein.

STATEMENT REGARDING FEDERALLY SPONSORED RESEARCH

Not Applicable.

FIELD OF THE INVENTION

The field of the invention is medical devices and methods for their use. More particularly, the invention relates to a prosthesis for a distal radioulnar joint and methods for its use.

BACKGROUND OF THE INVENTION

Figure 1:
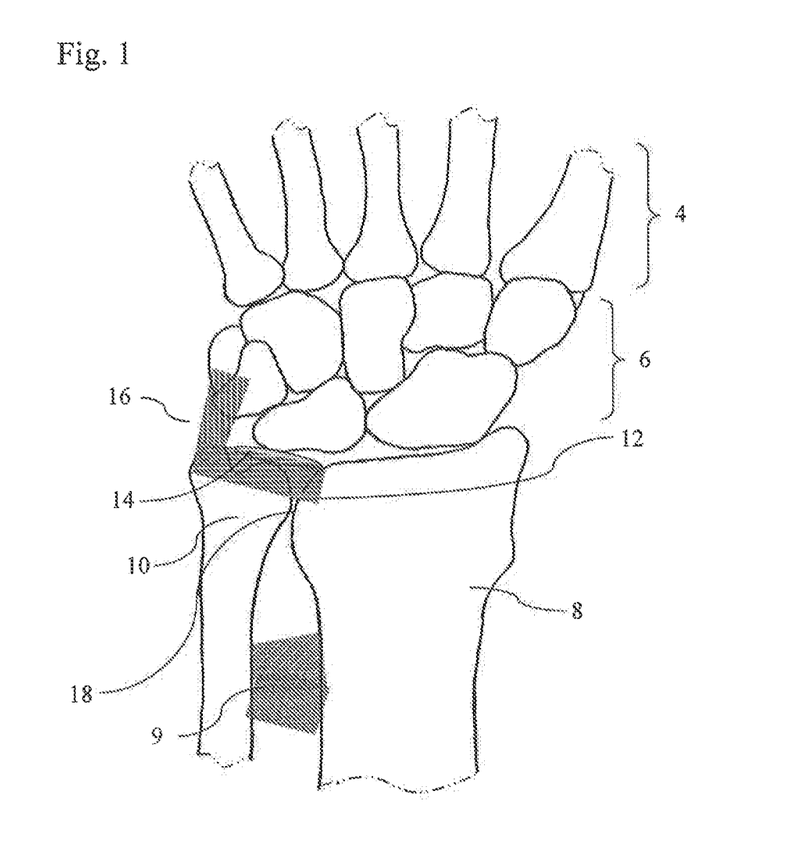
FIG. 1 is a view of the dorsal side of a patient's left hand and wrist illustrating the bone structure of the wrist in conjunction with the radius and the ulna.

The distal radioulnar joint (DRUJ) is an essential portion of the wrist that allows rotation or supination and pronation of the forearm. With reference to FIG. 1, the dorsal side of the bone structure of a patient's left proximal metacarpals 4 and carpals 6 is illustrated in conjunction with the radius 8 and the ulna 10. The radius 8 articulates in pronation and supination on the distal head of the ulna 10 at the sigmoid notch 12. The ulna 10, a slightly bowed bone linked to the wrist, translates dorsal-palmarly to accept the modestly bowed radius 8. Since the sigmoid notch 12 in most wrists is relatively flat, ligaments are required to support the distal ulna and the triangular fibrocartilage (TFC) discus 14, located where the ulna meets the wrist. Ligaments supporting the TFC include radioulnar ligaments (RULs) and ulnocarpal ligaments (UCLs). Together with the TFC, these ligaments form the triangular fibrocartilage complex (TFCC) 16, as depicted simplistically in FIG. 1. Additional support of the DRUJ is mediated by the interosseous membrane 9, a fibrous sheet connecting the radius 8 and the ulna 10. The DRUJ 18 can be thought of as having three degrees of motion: translation in the distal-proximal plane, rotation around the distal-proximal plane, and translation in the dorsal-palmar plane.

The movement and rotation of these bones enabled by support from the ligaments allows humans to open doors, turn screwdrivers, and many other common daily activities, Like any other joint in the body, the DUI can become significantly damaged through traumatic or degenerative destruction. Pain and dysfunction often follows any biomechanical disruption and patients eventually become debilitated and seek medical attention. Historically, this problem was treated with removing half of the joint and not restoring any anatomical structure, limiting the range of motion. In recent years however, implants have been designed to reconstruct the DRUJ.

The current prosthetic implants only allow two of the three degrees of motion: translation along the distal-proximal plane and rotation around the distal-proximal plane, but neither allow translation along the dorsal-palmar plane. Additionally, the current implants do not have the correct amount of constraint in their designs or require extremely precise alignment in order to provide proper motion. The ulnar stem is slightly bowed which has not been respected in current implant designs as all ulnar stem components are straight. This causes problems with insertion of the prosthetic implant as well as fixation and therefore long-term survival and loosening. Accordingly, there remains a need in the art for an improved DRUJ implant system that provides the stability and ranges of motion that mimic the healthy wrist.

SUMMARY OF THE INVENTION

The present invention overcomes the aforementioned drawbacks by providing a distal radioulnar joint prosthesis that utilizes articulating ulnar and radial components that are configured to preserve as much of the ligaments as possible. Such a device includes an ulnar component that has a stem to be inserted into the ulna, a collar, and a shell shaped to articulate with the radial component. The radial component has a plate shaped to be screwed to the radius in the sigmoid notch to maximize the contact between implant and bone. The radial component also has a hemi-spherical ball which allows for articulation with the distal end of the ulnar component. The hemispherical ball of the radial component articulates with the shell of the ulnar component via a motion liner.

Additional features of the ulnar component include a slightly bowed stem to match the slight bow of the ulna. The stem can be semi-flexible. The stem can have a titanium core. The titanium core of the stem can be made out of Nitinol. The stem can be coated with hydroxyapatite. The stem of the ulnar component has proximal and distal ends. The proximal end of the stem can have locking posts that can be deployed by rotation of a set screw at the distal end after the stem has been inserted into the ulna. The ulnar component includes a collar. The collar can be provided in various diameters and heights to provide a customized fit. The shell of the ulnar component can have holes for attaching suture for attaching the triangular fibrocartilage ligament. The shell of the ulnar component is generally shaped to receive the hemispherical ball of the radial component. The shell of the ulnar component can be an ellipsoid shape. The motion liner can serve as the interface for the interaction of the ulnar shell and the hemispherical ball. The hemispherical ball can be metal. The inner aspect of the hemisphere can have changing depths to allow for varying lengths in the radial-ulnar plane to optimize the tension and stability features of the interosseous membrane. A metal rod is attached to the inner aspect of the hemisphere to connect to the radial plate. The metal rod can connect to the radial plate via a Morse taper. The plate of the radial component can be shaped as a reverse triangle. The side of the radial plate that abuts against the radius can have a trabecular metal backing or a hydroxyapatite coating. The radial plate has screw holes to allow for attachment to the radius.

It is an aspect of the invention to provide a method for repairing the distal radioulnar joint. Such a method includes the steps of providing the device to a surgeon, the device generally including an ulnar component, a radial component, and a motion liner. An incision is made along the ulnar border of the distal forearm. The surgeon dissects down to the ulna and elevates the extensor carpi ulnaris (ECU) tendon and sheath away. The ulnar head is cut with an oscillating saw at the inferior aspect of the sigmoid notch, exposing the intramedullary canal and the soft tissues that formerly surrounded the distal ulna. These soft tissues include the TFCC. The distal ulna is flexibly reamed and the stem of the ulnar component of the prosthesis is tapped into the ulnar shaft. The ulnar stem is locked into place via rotation of the set screw. A collar reamer is used to smooth the end of the distal ulna. Trial collars are used to find the correct height for the ulnar shell. The collar of the ulnar component is screwed onto the set screw of the stem until the proximal surface of the collar contacts and seats on the ulna. The plate of the radial component of the prosthesis is placed against the sigmoid notch and used as a guide to put a K-wire through the center. A sigmoid notch reamer is then used to contour the sigmoid notch to the shape of the radial plate. The reamer has an attachment that hooks onto the set screw of the ulnar component so the correct angle and depth can be achieved. The radial plate is placed and the screws to attach the plate to the radius are drilled for and inserted into the radial metaphysis. Trial hemispheres are used to find the correct radial-ulnar length. The rod on the hemisphere with the appropriate length is inserted into the peg on the radial plate until the Morse taper is engaged. The liner is placed into the ulnar shell and the ulnar shell is placed on top of the collar so that the set screw enters the hollow shaft of the shell. Placing the ulnar shell onto the collar traps the hemispherical ball. The base of the ulnar shell is secured to the collar on the ulnar stem with screws. Ligaments of the TFCC are sutured to the ulnar shell and the incision is closed.

In one embodiment, the invention provides a distal radioulnar joint prosthesis including a radial component including a plate and hemispherical ball connected to the plate; an ulnar component including a stem defining distal and proximal ends, a collar, and a shell; and a motion liner dimensioned to be received in the shell and to be positioned over a surface of the ball. In one form, the stem of said ulnar component is expandable. In one form, the stem of said ulnar component includes one or more locking posts near the proximal end of said stem. Movement of the collar results in each locking post extending from the stem and engaging with the ulna. The ulnar component may include a set screw, and said collar and said shell can be attached to said stem by the set screw. In one form, the stem of said ulnar component is semi-flexible. The stem can include a titanium core and an outer layer of a superelastic material such as Nitinol. The stem can be coated with hydroxyapatite.

In one form, the outer layer of the stem comprises spiraling sheets. The ulnar component can include a set screw, and rotation of the set screw causes the spiraling sheets to separate. In one form, the spiraling sheets separate such that the separated spiraling sheets are against endosteal bone. In one form, the stem of said ulnar component is bowed. In one form, the plate of said radial component has a reverse triangular shape. In one form, the shell is ellipsoid. The hemispherical ball can be connected to the plate by a rod. In one form, the rod has a length that is adjustable. In one form, the prosthesis has a concave articulating surface including a major radius of curvature and a minor radius of curvature.

The prosthesis can have a concave articulating surface that contacts the ball when the prosthesis is implanted in the distal radioulnar joint. The concave articulating surface is larger than the ball by a first distance in a distal-proximal plane of the distal radioulnar joint, and the concave articulating surface is larger than the ball by a second distance in a dorsal-palmar plane of the distal radioulnar joint when the prosthesis is implanted in the distal radioulnar joint. The second distance can be greater than the first distance.

The prosthesis allows for translation along a distal-proximal plane of the distal radioulnar joint, and rotation around a distal-proximal plane of the distal radioulnar joint, and translation along a dorsal-palmar plane of the distal radioulnar joint when the prosthesis is implanted in the distal radioulnar joint. When the wrist supinates, the ball can translate palmar, and when the wrist pronates, the ball can translate dorsal.

In another embodiment, the invention provides a method of implanting a prosthesis to replace the distal radioulnar joint. The may include the steps of (a) selecting an ulnar component, the ulnar component having a stem, a collar, and a shell; (b) selecting a radial component, the radial component having a plate and a hemispherical ball; (c) inserting the stem of the ulnar component into the intramedullary canal of the ulna; (d) screwing the collar onto a set screw of the stem; (e) securing the plate of the radial component at the sigmoid notch of the radius; (f) attaching the hemispherical ball of the radial component to the radial plate; (g) fitting the motion liner of the radial component into the shell; and (h) attaching the shell of the ulnar component to the collar of the ulnar component such that the hemispherical ball articulates with the shell via the motion liner.

In yet another embodiment, the invention provides a method of implanting a prosthesis to replace the distal radioulnar joint. The may include the steps of (a) selecting an ulnar component, the ulnar component having a stem, a collar, and a shell; (b) selecting a radial component, the radial component having a plate and a hemispherical ball; (c) inserting the stem of the ulnar component into the intramedullary canal of the ulna; (d) screwing the collar onto a set screw of the stem; (e) securing the plate of the radial component at the sigmoid notch of the radius; (f) attaching the hemispherical ball of the radial component to the radial plate; (g) fitting the motion liner over the hemispherical ball of the radial component; and (h) attaching the shell of the ulnar component to the collar of the ulnar component such that the hemispherical ball and motion liner articulate with the shell.

The foregoing and other aspects and advantages of the invention will appear from the following description. In the description, reference is made to the accompanying drawings which form a part hereof, and in which there is shown by way of illustration an exemplary embodiment of the invention. Such embodiment does not necessarily represent the full scope of the invention, however, and reference is made therefore to the claims and herein for interpreting the scope of the invention.

Like reference numerals will be used to refer to like parts from Figure to Figure in the following description of the drawings.

DETAILED DESCRIPTION OF THE INVENTION

Figure 2:
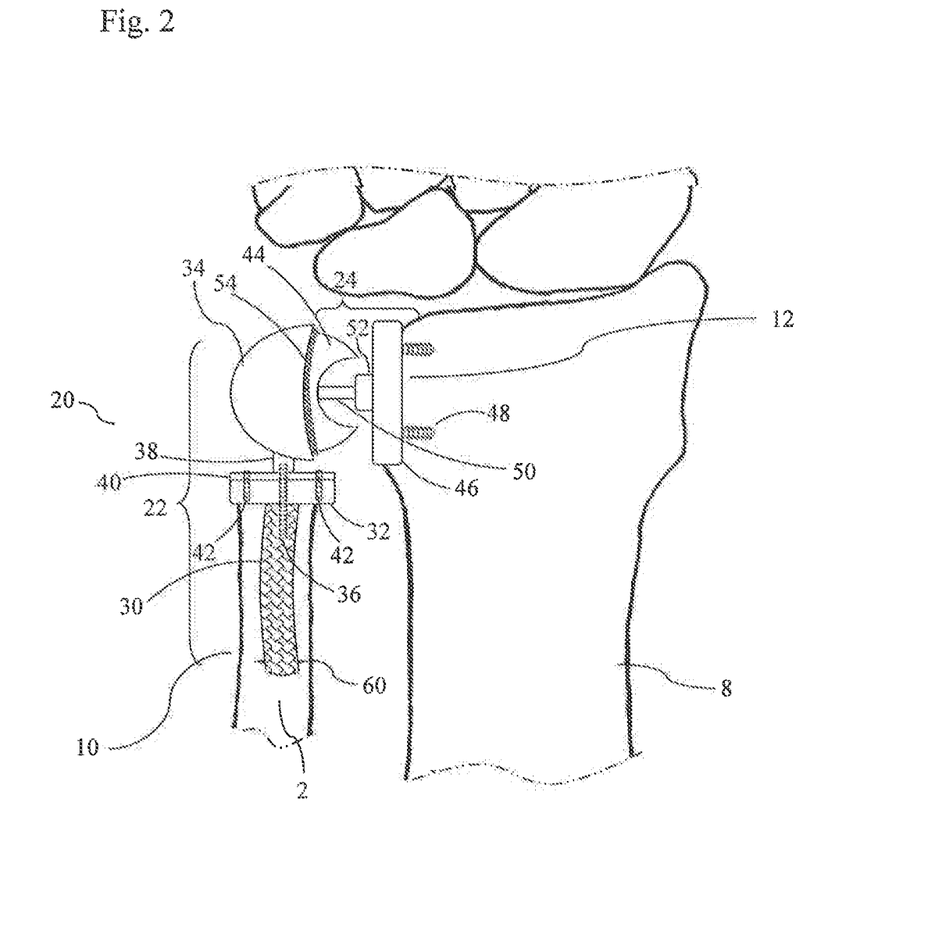
FIG. 2 is a dorsal skeletal view of the human left forearm after implantation of a distal radioulnar joint prosthesis in accordance with the present invention.

FIG. 2 illustrates an exemplary distal radioulnar joint (DRUJ) prosthesis that has been implanted in accordance with the present invention. The DRUJ prosthesis 20 generally includes an ulnar component 22 and a radial component 24. The ulnar component 22 includes a stem 30, a collar 32, and a shell 34. The stem 30 has a central set screw 36, The set screw 36 serves as the connector for the stem 30, collar 32, and shell 34. The shell 34 has a shaft 38 that connects the shell 34 to the shell base 40 that is capable of receiving the set screw 36 and coupling to the collar 32. The shell base 40 is attached to the collar 32 by screws 42. The shell 34 allows for coupling with the radial component 24. The radial component 24 includes a hemispherical ball 44 and a plate 46. The plate 46 is secured to the radius 8 at the sigmoid notch 12 via bone screws 48, The hemispherical ball 44 has a rod 50 that couples to a peg 52 on the plate 46. The hemispherical ball 44 couples with the shell 34 of the ulnar component 22 with a motion liner 54 serving as the interface between the hemispherical ball 44 and the shell 34. For the present invention, the ulnar component 22 is intended to replace at least a portion of the distal ulna 10, For the present invention, the radial component 24 is intended to replace at least a portion of the sigmoid notch 12.

Figure 3:
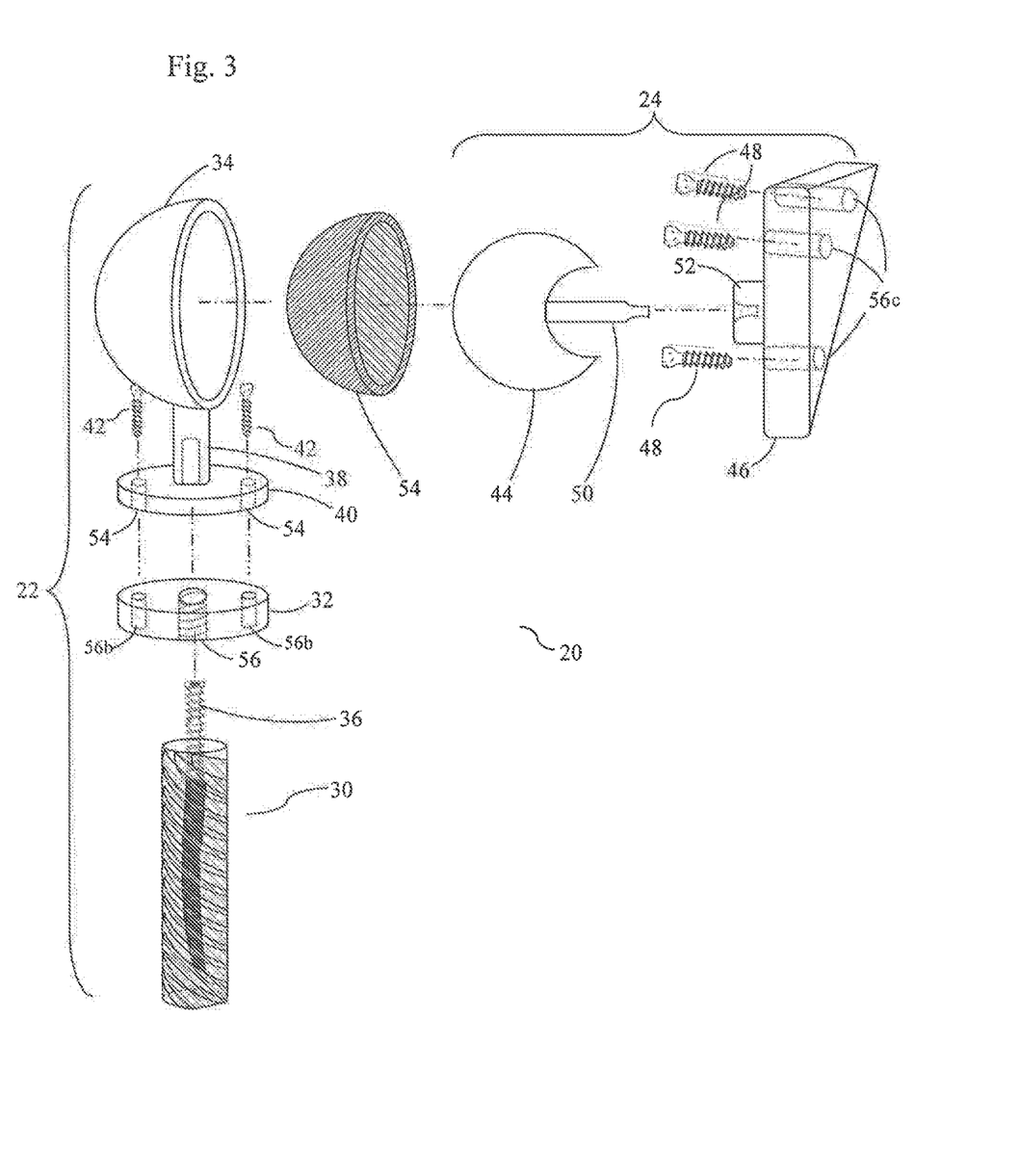
FIG. 3 is an exploded perspective view of the distal radioulnar joint prosthesis of FIG. 2.

FIG. 3 depicts the ulnar component 22 and the radial component 24 of the DRUJ prosthesis 20 prior to implantation. The stem 30 has a central set screw 36 that allows for the distal end of stem 30 to couple to a collar 32. In the center of the collar 32, there is a threaded hole 56 allowing for the collar 32 to couple to the stem 30 via the set screw 36. The set screw 36 of stem 30 passes through the threaded hole 56 in the center of the collar 32 and fits into the hollow shaft 38 of the shell 34. The hollow shaft 38 of the shell 34 is sufficiently hollow in order to accommodate the set screw 36 without the set screw 36 needing to be screwed into the shaft 38. The base 40 of shell 34 is shaped so that it matches the shape of the collar 32. Both the shell base 40 and the collar 32 have threaded screw holes 54, 56b so the two pieces can be secured with screws 42. The shell 34 allows for coupling with the radial component 24. The radial component 24 includes a hemispherical ball 44 and a plate 46. The plate 46 has threaded holes 56c so it can be secured to the radius 8 at the sigmoid notch 12 via screws 48. The plate 46 has a peg 52 that is capable of receiving the rod 50 of the hemispherical ball 44. The hemispherical ball 44 couples with the shell 34 of the ulnar component 22 with a motion liner 54 serving as the interface between the hemispherical ball 44 and shell 34.

Figure 4A:
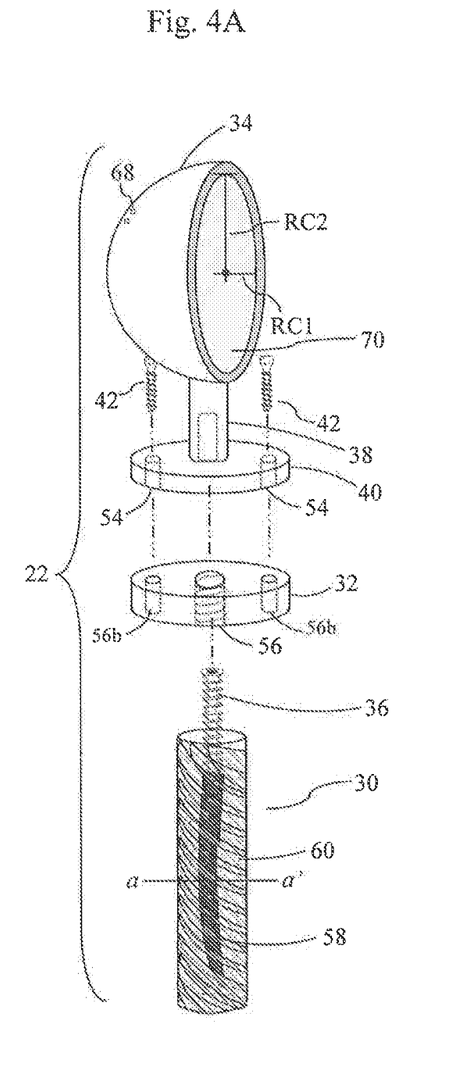
FIG. 4A is an exploded perspective view of the ulnar component of the distal radioulnar joint prosthesis of FIG. 2.

FIG. 4A depicts the ulnar component 22. Unlike current implants that do not account for the slight bow of the ulna, the stem 30 of the DRUJ prosthesis 20 of the present invention will be constructed such that it is semi-flexible and can bow to match the natural bow of the ulna 10 once implanted, regardless of the initial provided shape. The semi-flexible design is obtained by utilizing a titanium core 58 and a layer 60 of spiraling sheets of Nitinol for the construction of the stem 30. The proximal end of the set screw 36 of the stem 30 is connected to the distal end of a titanium core 58. The proximal end of the titanium core is connected to the spiraling sheets of alloy near the proximal end of the stem 30 (connection not shown). The length of the titanium core can be between about 40 millimeters and about 50 millimeters. The total length of the stem can be between about 50 millimeters and about 60 millimeters. The titanium core 58 can be shaped with a slight bow to match the average bow of the ulna, as shown in FIG. 4A. Alternatively, the titanium core 58 can be straight prior to implantation but thin enough so it can flex with the stem 30 after it is implanted and conforms to the natural bow of the ulna 10.

Figure 4B:
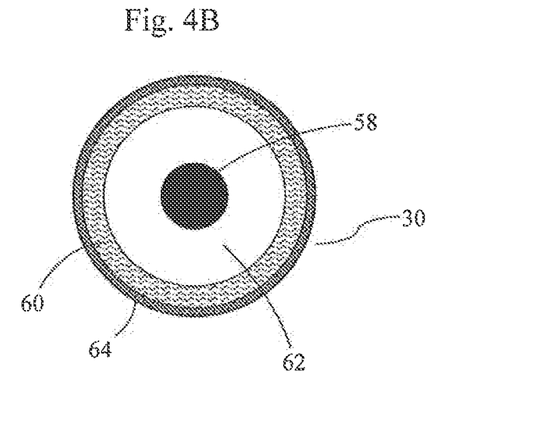
FIG. 4B is cross sectional view of the stem of the ulnar component of FIG. 2 taken along line a-a' of FIG. 4A.

The semi-flexible design can be obtained by utilizing the stem 30 configuration as seen in the enlarged cross sectional view in FIG. 4B taken at line a-a' in FIG. 4A. The titanium core 58 can have a diameter between about 3 millimeters and about 10 millimeters. The titanium core 58 has a diameter such that it does not prevent the stem 30 from being flexible. Alternatively, the titanium core can be a hollow. The outer edge of the stem 30 is made of spiraling sheets of an alloy. The alloy will be a composition such that the stiffness versus elasticity allows the implant to most closely follow the endosteal surface of the bone, Preferably, the sheets of layer 60 will be made of Nitinol, a superelastic nickel titanium alloy. The alloy layer 60 will have a wall thickness between about 1 millimeters and about 3 millimeters. In a preferred embodiment, the alloy layer 60 is made of spiraling sheets of Nitinol that are closely aligned. The space 62 between the titanium core 58 and the alloy layer 60 can be hollow. The alloy can have a coating 64 to enhance bone integration. The coating 64 can be a hydroxyapatite layer or a commercially pure titanium plasma coating.

Referring back to FIG. 4A, the ulnar component includes a stem 30, collar 32, and shell 34. Stem 30 is intended to be inserted into the intramedullary canal 2 of the ulna. The stem 30 is generally cylindrical in shape. In some cases, stem 30 can be tapered near the proximal end such that the shape is generally conical. The stem 30 as depicted in FIG. 4A has a slightly bowed inner titanium core 58, but has an outer shape that is straight prior to implantation. In some cases, the ulnar stem 30 provided may have a slight bow prior to implantation. Stem 30 has a central set screw 36. The set screw 36 is used as a connector for the collar 32 and the shell 34. The set screw can have a length of between about 5 millimeters to about 20 millimeters. When the stem 30 has been inserted into the intramedullary canal 2 of the ulna, the collar 32 can be screwed onto the set screw 36 through the threaded hole 56 in the center of the collar 32. The collar 32 can be screwed until the proximal surface of the collar 32 rests on the distal end of the ulna. The remaining portion of the set screw 56 can be fitted into the shaft 38 of the shell 34, allowing for the shell base 40 to rest on the proximal surface of the collar 32. The shell base 40 and collar 32 can be secured together. As shown in FIG. 4A, the stem base 40 and collar 32 can have threaded screw holes 54, 56*b* for screws 42 to secure the stem base 40 to the collar 34. Although holes 56*b* that can accommodate two screws 42 are shown, there can be more threaded screw holes 56*b*. For example, there can be holes to accommodate three, four, five, or six screws. In some cases, the collar can rest against the distal end of the ulna 10 without bone cement. The collar 32 can have a coating on the surface that rests against the ulna 10 that promotes bone integration. For example, the coating can be a hydroxyapatite layer or a commercially pure titanium coating. The collar 32 can have a diameter between about 10 millimeters and about 40 millimeters. The collar height can be between about 1 millimeters and about 10 millimeters.

Figure 4C:
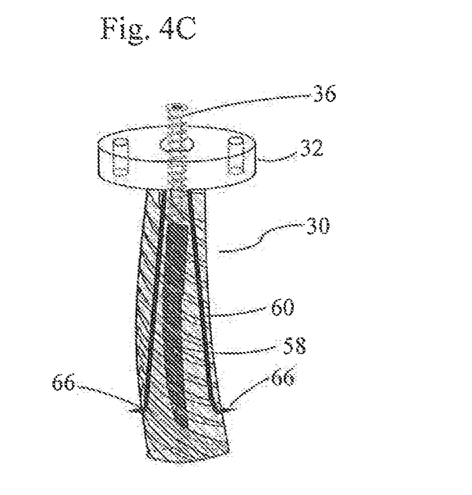
FIG. 4C is a perspective view of the ulnar stem and collar of the distal radioulnar joint prosthesis of FIG. 2 after it has been implanted into the ulna.

After the stem 30 has been tapped into the ulna until the proximal surface of collar 32 contacts the distal end of the ulna, the set screw 36 can be rotated counter-clockwise to initiate axial expansion of stem 30 and lock stem 30 in place within the intramedullary canal of the ulna. Referring now to FIG. 4C, counter-clockwise rotation of set screw 36 causes the set screw to migrate distally and protrude slightly further from the stem 30. Since the proximal end of the set screw 36 is connected to the distal end of the titanium core 58 and the proximal end of the titanium core 58 is connected to the alloy layer 60, counter-clockwise rotation of the set screw 36 causes the spiraling sheets of alloy layer 60 to separate slightly, allowing circumferential stress, or hoop stresses, against the endosteal bone. The expansion also aids in locking the stem 30 in place. The circumferential stress combined with the hydroxyapatite coating 64 of the stem 30 will ignite a bony response. The bony response results in faster and stronger fixation. The set screw 36 can be turned approximately a quarter turn, a half turn, or an entire turn to obtain the appropriate amount of expansion for a tight, secure fit.

Both FIGS. 3 and 4A show the stem 30 prior to implantation and expansion. FIG. 4C demonstrates how the stem 30 could appear after implantation and expansion by counter-clockwise rotation of the set screw. To further secure the stem 30 in the intramedullary canal of the ulna, the stem 30 may optionally have locking posts 66. The locking posts 66 can extend from the exterior of the stem 30 such that the locking posts 66 engage with the ulna. Although only two locking posts 66 are shown in FIG. 4C, there can be more than two locking posts. For example, there can be three, four, five, or six locking posts. In other cases, there can be no locking posts. In one embodiment, the locking posts are deployed as the collar 32 is screwed onto the stem 30 via the set screw 36. For example, in FIG. 4C, screwing of the collar 32 onto the set screw 36 can apply force to the distal end of the locking posts 66, resulting in the locking post extending from the stem 30 and engaging with the ulna (not shown). Although the locking posts 66 are shown extending from the proximal end of the stem 30, the locking posts 66 could extend from the stem 30 at any point along the length of the stem 30.

Referring back to FIG. 4A, the shell 34 has a shaft 38 to engage with the set screw 36. The shaft 38 is sufficiently hollow to accommodate the set screw 36 providing a tight fit, but not tight enough to require threading. The hollow shaft is wide enough so that it can be placed over the set screw 36 without the need for any screwing. The shell 34 is preferably made of metal, for example, pure titanium. The shell could also be made of a chrome-based alloy, titanium alloy and hard-coated with titanium nitride or ion-implanted for increased wear resistance. The thickness of the metal that forms the shell 34 can be between about 1 millimeters and about 10 millimeters. In some cases, the shell 34 is formed with suture holes 68. Suture holes 68 can be used to attach soft tissue to the shell 34. Although only two suture holes 68 are shown, it is to be appreciated that any number of suture holes 68 can be used in accordance with the present invention.

The shell 34 is shaped such that it generally matches the curvature of the hemispherical ball 44 to provide a close sliding fit, but is slightly ellipsoidal. The generally ellipsoid shape at the articulating surface can help recreate normal kinematics. The concave articulating surface 70 of the shell 34 defines two radii, a major radius of curvature RC1 and a minor radius of curvature RC2, as shown in FIG. 4A. RC1 can be between about 4 millimeters and about 8 millimeters. RC2 can be between about 4 millimeters and about 8 millimeters. The dimensions of the hemispherical ball 58 will be discussed below. To allow for low-friction movement between the shell 34 and hemispherical ball 44, a motion liner 54 is tightly fitted into the shell 34. Because the motion liner 54 is tightly fitted into the shell 34 in this version of the DRUJ prosthesis 20, the motion liner 54 does not move with respect to the shell 34 and the hemispherical ball 44 articulates with the motion liner 54. Motion liner 54 is made out of a material that allows for smooth movement, provides a thermal break, and minimizes wear on the metal components. The motion liner 54 can be made of a polymeric material. For example, the polymeric material can be ultra high molecular weight polyethylene. The thickness of the motion liner 54 can be between about 1 millimeters and about 5 millimeters. In a preferred embodiment, the motion liner 54 is press-fit into the shell 34. Alternatively, the motion liner 54 can be press-fit over the hemispherical ball 44. As with the shell 38, the liner 54 is generally shaped such to match and accommodate the curvature of the hemispherical ball 44. Because the motion liner 54 is press-fit over the hemispherical ball 44 in this alternative version of the DRUJ prosthesis 20, the motion liner 54 articulates with the shell 34, and the hemispherical ball 44 does not move with respect to the motion liner 54.

Figure 5A:
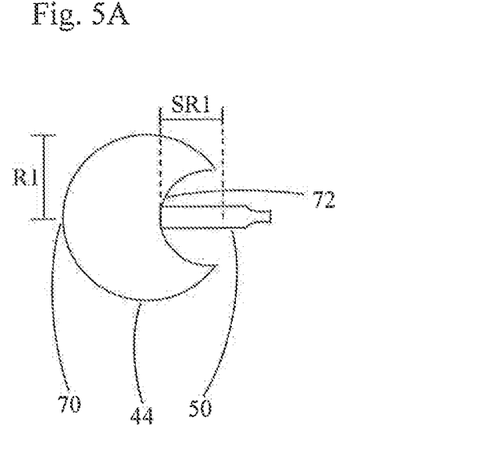
FIG. 5A is a side view of the hemispherical ball fitting into the ulnar shell of the distal radioulnar joint prosthesis of FIG. 2.
Figure 5B:
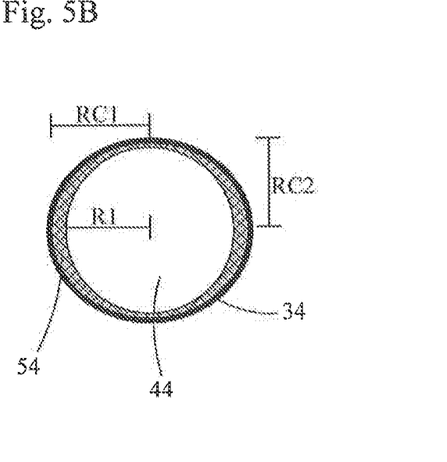
FIG. 5B is a side view of the convex articulating surface of the hemispherical ball of FIG. 5A.

Referring now to FIG. 5A, the hemispherical ball 44 is preferably made out of metal. For example, the metal could be titanium, titanium-based alloy, or chrome-based alloy. The hemispherical ball 44 has a slightly ellipsoidal in shape at a convex articular surface 70. The radius, R1 of the hemispherical ball 44 can be between about 2 millimeters and about 6 millimeters. The radius of curvature generally matches the curvature and dimensions of the motion liner 54 and shell 34 to provide a close sliding fit. FIG. 5B shows how the hemispherical ball 44 fits into the shell 34 that has been fitted with a motion liner.

The generally ellipsoid-shaped shell 34 and liner 54 is approximately 1 millimeters larger in the distal-proximal plane (RC2 of shell 34 is greater than R1 of hemispherical ball 44) and approximately 4 millimeters larger in the dorsal-palmar plane (RC1 of shell 34 is greater than R1 of hemispherical ball 44). The generally ellipsoid shape at the articulating surface 70 can help to recreate normal kinematics.

The DRUJ prosthesis 20 of the present invention will allow the anatomy and biomechanics of the interosseous membrane to be preserved and respected by keeping this structure adequately tensioned and stabilized. This can be accomplished through altering the distance between the plate 46 and hemispherical ball 44. As shown in FIG. 5A, the hemispherical ball 44 has a secondary spherical radius SR1, defining the concave back surface 72. In one embodiment, the length of the rod 50 is fixed and the concave back surface 72 of hemispherical ball 44 has changing depths to allow for varying lengths in the radial-ulnar plane. SR1 can be between about 1 millimeters and about 5 millimeters. In a preferred embodiment, the length of rod 50 is variable and customized depths in the radial-ulnar plane is accomplished by providing hemispherical balls 44 with rods 50 of varying lengths. In another embodiment, the length of the rod 50 is adjustable and the length can be customized intra-operatively. The length of rod 50 can be between from about 3 millimeters to about 20 millimeters. The rod 50 extends from the center of the concave back surface 72 and articulates with the peg 52 on the radial plate 46. In the exemplary embodiment, the rod 50 articulates with peg 52 via a Morse taper.

Figure 6A:
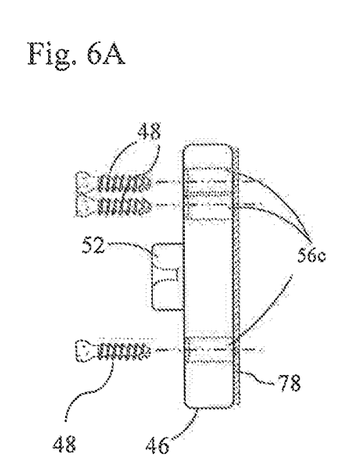
FIG. 6A is an exploded side view of the radial plate of the distal radioulnar joint prosthesis of FIG. 2.
Figure 6B:
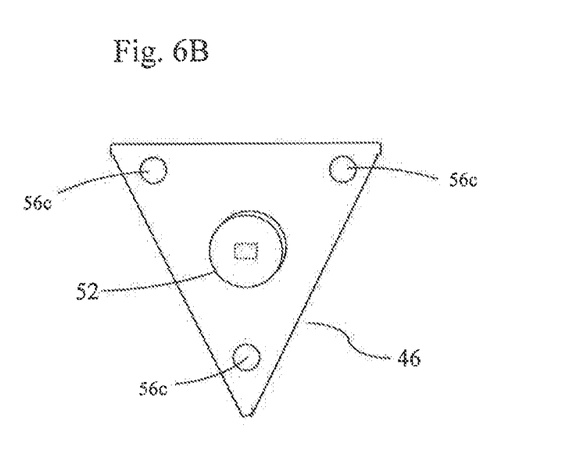
FIG. 6B is an exploded frontal view of the radial plate of FIG. 6A, showing the side of the plate that is capable of articulating with the hemispherical ball.

The radial plate 46 of the DRUJ prosthesis 20 is generally made of metal. The metal is titanium, titanium-based alloy, or chrome-based alloy. The plate 46 can be any shape that is compatible with the shape of the sigmoid notch. The radial plate 46 will stop just proximal to the distal oblique bundle of interosseous membrane in order to keep the interosseous membrane intact. In an exemplary embodiment, shown in FIG. 6B, the plate 46 is generally a reverse triangular shape. Regardless of shape, the height of the plate 46 can be between 5 millimeters and 20 millimeters. The maximum width of the plate 46 can be between 5 millimeters and 10 millimeters. The thickness of the plate 46 as shown in the side view in FIG. 6A can be between 3 millimeters and 10 millimeters. The corners of the plate 46 can be rounded to accommodate the sigmoid notch of the radius and allow maximal contact between the plate 46 and the bone. The plate 46 has threaded screw holes 56c so that the plate 46 can be screwed to the radius. Although three holes are exemplary, the plate 46 can include any number of screw holes. For example, the plate 46 can have two, three, four, five or six screw holes. Bone screws 48 can be used to screw the plate 46 to the radius. While the screws 48 pictured in FIG. 6A are shown as perpendicular to the plate 46, in an exemplary embodiment (not shown), the screws can be directed proximally and at differing angles to allow for bicortical fixation in the radial metaphysis. Angling the screws will enable the use of longer screws, increase the pull-out strength, and resist torsional stress place on the construct. The back surface of the plate 46 that articulates with the sigmoid notch of the radius can have a coating 64. The coating 64 enhances bone integration. For example, the coating 64 can be a hydroxyapatite layer or a commercially pure titanium plasma coating. In some cases the coating is the same as the coating on the ulnar stem 30. In some cases, the coating on the radial plate 46 is a different coating than the coating on the ulnar stem. The radial plate 46 includes a peg 52 which is generally near the center of the plate 46. The peg 52 is shaped so it is able to articulate with the rod 50 of the hemispherical ball 44. Although any connection means can be used, in an exemplary embodiment, the peg 52 and rod 50 are connected via a Morse taper.

Figure 7:
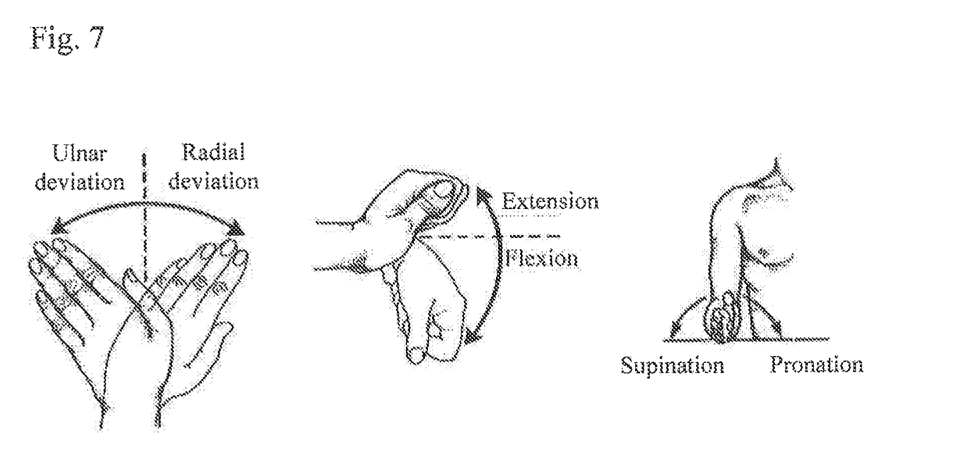
FIG. 7 is a pictorial representation of the motions of the normal wrist that will be supported by the distal radioulnar joint prosthesis of the present invention.
Figure 8:
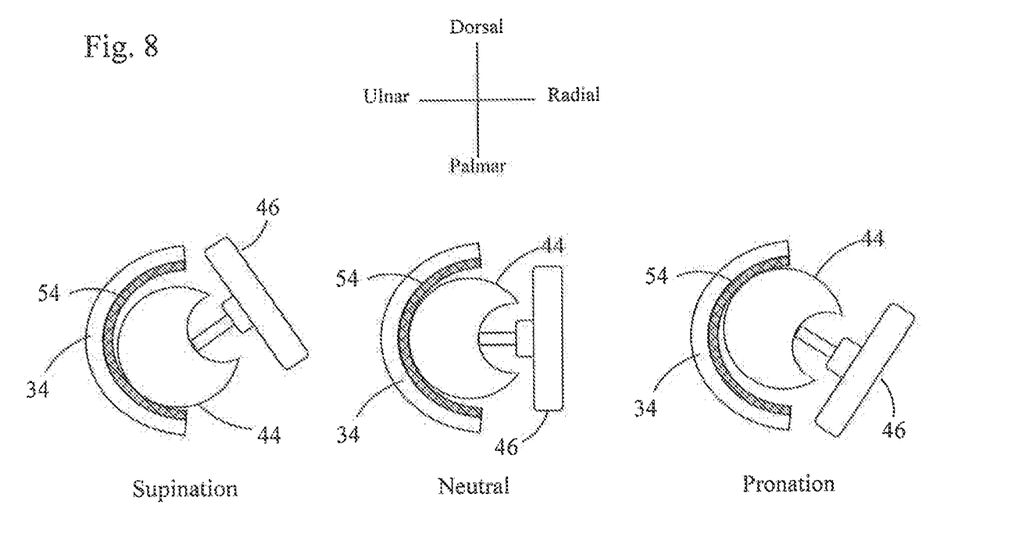
FIG. 8 depicts the supination, neutral, and pronation of the primary articulation of an embodiment of the present invention.

The motion of the DRUJ prosthesis 20 will allow freedom of rotation and translation but also provide necessary stability. The nearly 160 degrees of rotation will be accomplished at the interface between the motion liner 54 and hemispherical ball 44. As described above, the liner 54 and shell 34 will be closely matched in size for stability so only rotation occurs and no translation in the radio-ulnar plane. The translation part of motion will occur at the interface between the motion liner 54 and the hemispherical ball 44. As discussed above, the hemispherical ball 44 will have a diameter that is approximately 4 millimeters smaller in the dorsal-palmar plane and approximately 1 millimeters smaller in the distal-proximal plane than the generally ellipsoid shape of the shell 34 and motion liner 54. Therefore, as the wrist moves in pronation-supination, all three degrees of motion will be accomplished. FIG. 7 depicts the normal wrist motions that will be allowed by the DRUJ prosthesis 20 of the present invention. The wrist can move in radioulnar deviation as well as flexion-extension through the radiocarpal joint. Pronation-supination occurs solely at the distal radioulnar joint. FIG. 8 depicts the movement of certain components of the DRUJ prosthesis 20 when the wrist is in neutral position, supination, and pronation. For clarity, only the shell 34 and pieces of the radial component 24 are shown. As the wrist supinates, the hemispherical ball 44 translates palmar. As the wrist pronates, the hemispherical ball 44 translates dorsal. This illustrates the ability of the DRUJ prosthesis 20 to mimic the kinematics of natural wrist motion, allowing for freedom of motion in a semi-constrained manner. The DRUJ prosthesis 20 of the present invention will allow for forearm rotation of about 150° to about 170°.

Figure 9:
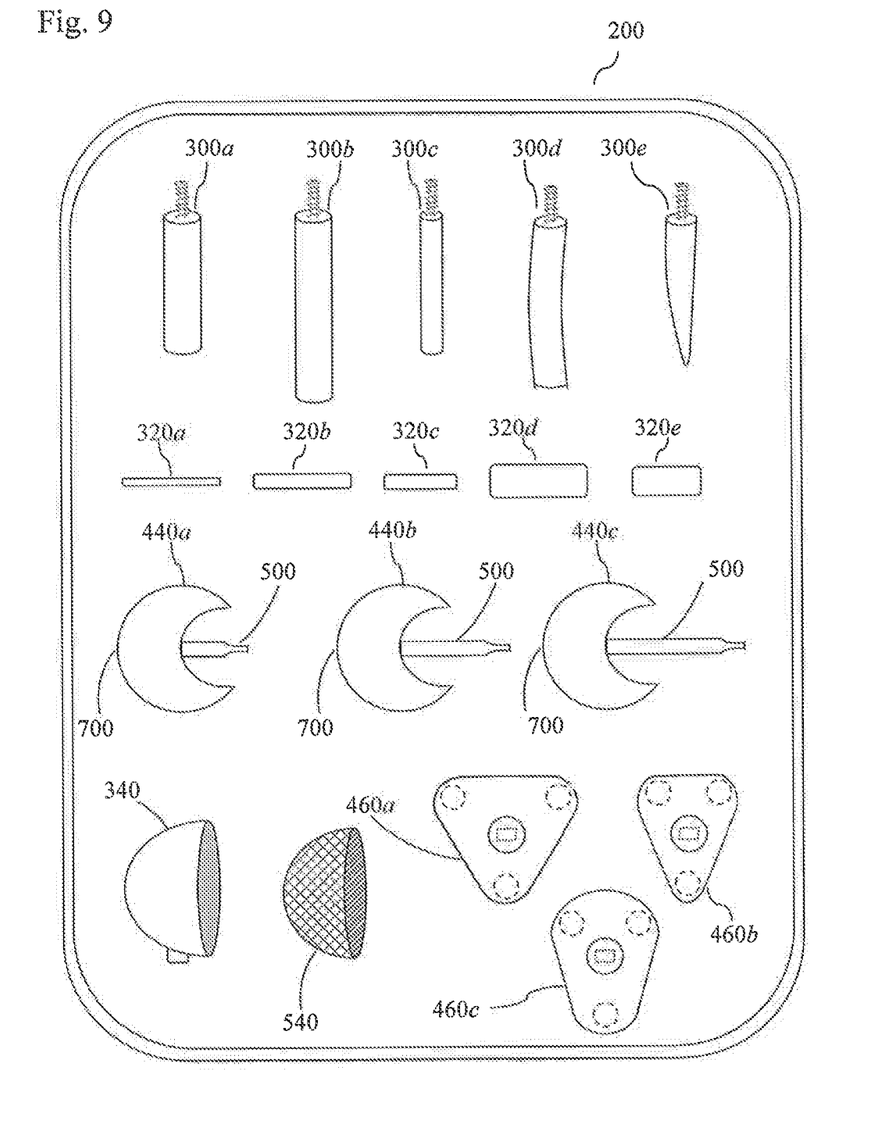
FIG. 9 is a kit view of various embodiments of the present invention.

It will be understood that each of the exemplary embodiments of the components of the DRUJ prosthesis may include portions that are substantially dissimilar from the selected exemplary embodiments and may include combinations of each of the various embodiments. Therefore, the exemplary embodiments are not intended to limit the scope of the following claims but merely are provided to exemplify the portions thereof. Therefore, with reference to FIG. 9, the kit 200 or supply may include a plurality of the stem portion 300a, 300b, 300c, 300d, 300e, that each includes a selected unique dimension, such as length, width, or radius of curvature/degree of bowing. The kit 200 can also supply collars 320 that have various diameters and heights. Furthermore, the kit 200 may provide a plurality of hemispherical balls 440a, 440b, 440c. Although it should be understood that the hemispherical balls provided could have fixed length rods and varying radii of curvature of the concave back surface to provide a customized distance between the ulna and radius, the hemispherical balls 440 in the kit 200 shown are provided with rods 500 of varying lengths and a fixed radius of curvature of the concave back surface. The convex articulating surface 700 is the same curvature on all hemispherical balls 440 provided such that the convex articulating surface 700 is compatible with the motion liner 540 and ulnar shell 340. In some cases, the motion liner 540 may be provided already press fit into shell 340. The kit 200 may also provide a plurality of radial plates 460a, 460b, 460c in various sizes or shapes. Each may be provided in a large inventory or in a kit 200 for selection by a user substantially intraoperatively or preoperatively. Nevertheless, various sizes or configuration of the stem 300, collar 320, radial plate 460, and rod 500 may be provided to allow for a substantially customized fit to a selected patient.

A pre-operative assessment using an x-ray template should be made to approximate the size of the DRUJ prosthesis 20. A dorsal incision is made through soft tissues to approach the ulna. The incision can provide access to the ulna 10 near the region of the distal radioulnar joint 18. After the incision has been formed, it can be augmented with various instruments, such as a retractor. The incision can therefore be made into any appropriate dimension, but can initially be formed in an appropriate dimension to achieve access to the ulna 10 for resecting a portion of the ulna 10 and implanting a selected DRUJ prosthesis 20. For example the incision can be a length from about 5 centimeters to about 10 centimeters. The incision is preferably centered over the distal radioulnar joint 18 in line with the fourth metacarpal when the forearm is in pronation. After the incision is formed, any appropriate resecting instrument, such as a saw that is interconnected with an appropriate motor can be used to resect a selected portion of the ulna 10. The ulna 10 can be resected any appropriate amount. The ulna 10 is preferably resected such that the distal end of the resected ulna 10 aligns with the sigmoid notch 12 on the radius.

After the ulna 10 has been resected a selected amount, various preparatory steps can be performed to allow for implantation of the DRUJ prosthesis 20. For example, the intramedullary canal 2 of the ulna 10 can be reamed with any appropriate tool to allow for application of the stem 30 into the ulna 10. Preferably, a flexible reaming tool is used. Prior to implantation of the prosthesis 20, a trial stem, trial collar, and trial shell (not shown) can be inserted and tested to verify anatomical alignment and to ensure that the proper resection length has been achieved. The stem 30 can be selected from the various sizes provided in the kit 200 based upon the anatomy of the patient. After removal of the trial stem, trial collar, and trial shell, the stem 30 of the prosthesis 20 can be inserted into the intramedullary canal 2 of the ulna 10 with or without various other materials, such as antibiotics, adhesives, bone cements or the like. Alternatively, or in addition thereto, the stem 30 can be driven or impacted into the intramedullary canal 2 of the ulna 10 without any preparation. The stem 30 is driven into the ulna 10 until it is flush with the distal end of the ulna 10. In some cases, a collar 32 can be screwed onto the top of the set screw 36 to provide a larger surface area for driving the stem 30 into the ulna 10. After the stem 30 has been driven into the ulna 10, the set screw 36 on the distal end of the stem 30 is rotated counter-clockwise. Counter-clockwise rotation of set screw 36 locks the stem 30 into position within the ulna 10. As the set screw 36 is rotated, the stem 30 expands radially, causing the outer sheets of alloy layer 60 (e.g., Nitinol) to slightly separate. The set screw 36 can continue to be rotated until there is satisfactory compression between the stem 30 and ulnar bone 10. Next, a collar reamer can be used to smooth the end of the distal ulna 10, The collar 32 is screwed onto the set screw 36 of the stem 30 until it is seated on top of the distal ulna. If a stem 30 with locking posts 66 is selected, screwing on the collar 32 also results in the deployment of locking posts 66 extending out of the stem 30 and engaging with the ulna 10.

A trial radial plate (not shown) can be placed against the sigmoid notch 12 and used as a guide to put a K-wire through the center of the trial plate. A radial plate 46 can be selected from the various sizes and shapes provided in kit 200 based on the anatomy of the patient. After the appropriate plate 46 has been selected, the sigmoid notch 12 can be reamed with a sigmoid notch reamer to contour the sigmoid notch 12 to the shape of the radial plate 46. The sigmoid notch reamer (not shown) has an attachment that can connect to the set screw 36 and rest on the collar 32 to assist with appropriate alignment. The sigmoid notch reamer can be attached to the set screw 36 such that the correct angle and depth of reaming can be achieved. After the sigmoid notch 12 is reamed to accommodate the plate 46, the radial plate 46 will be placed so that holes for the bone screws 48 can be measured and drilled. The bone screws 48 are then inserted through the screw holes 56c on the radial plate 46 into the radial metaphysis. The sigmoid notch reamer can be removed from the ulnar stem 30 any time after the alignment radial plate 46 has been determined.

As discussed above, the hemispherical ball 44 can be provided in a plurality of radii of the concave back surface 72. A trial hemispherical ball (not shown) can be used in combination with a trial shell (not shown) and trial motion liner (not shown) to find the appropriate hemispherical ball 44 that provides the optimum radial-ulnar distance to keep the interosseous membrane 9 at the correct tension. Alternatively, instead of hemispherical balls 44 that have a plurality of rod lengths 50, hemispherical ball 44 can be provided that have different radii of curvature of the concave back surface 72. Once the hemispherical ball 44 is selected that provides the appropriate radial-ulnar distance, the hemispherical ball 44 can be attached to the radial plate 46 via the rod 50 and peg 52. If the connection is via a Morse taper, the rod 50 of the hemispherical ball 44 can be connected to the peg 52 using a tap to engage the Morse taper.

After the hemispherical ball 44 is connected to the radial plate 46, the motion liner 54 can be press fit into the shell 34. Alternatively, the motion liner 54 can be press-fit over the hemispherical ball 44 of the radial component. The ulnar shell 38 can be placed over the collar 32 such that the set screw 36 enters the hollow shaft 38 and the shell base 40 is aligned over the collar 32. Screws 42 are inserted into the screw holes 56b of the shell base 40 and screwed into the collar 32. Finally, the ligaments of the TFCC 16 and other soft tissue can be attached using the suture holes 68 on the ulnar shell 34 and the subcutaneous tissues and skin can be closed over the DRUJ prosthesis 20.

Thus, the invention provides a prosthesis for a distal radioulnar joint wherein the prosthesis allows for three degrees of motion: translation along the distal-proximal plane, rotation around the distal-proximal plane, and translation along the dorsal-palmar plane.

The present invention has been described in terms of one or more exemplary embodiments, and it should be appreciated that many equivalents, alternatives, variations, and modifications, aside from those expressly stated, are possible and within the scope of the invention.

The invention claimed is:

1. A distal radioulnar joint prosthesis, comprising:
   a radial component including a plate and hemispherical ball connected to the plate;
   an ulnar component including a stem defining distal and proximal ends, a collar releasably engaged with the stem, and a shell coupled to the collar and configured with an opening facing a radius bone when the prosthesis is implanted in the distal radioulnar joint; and
   a motion liner dimensioned to be received in the shell and to be positioned over a surface of the ball.

2. A distal radioulnar joint prosthesis as recited in claim 1, wherein said stem of said ulnar component is expandable.

3. A distal radioulnar joint prosthesis as recited in claim 1, wherein said stem of said ulnar component includes one or more locking posts near the proximal end of said stem.

4. A distal radioulnar joint prosthesis as recited in claim 3, wherein said ulnar component includes a set screw dimensioned to be received in the stem, and rotation of the collar causes the set screw to engage the locking posts and results in each locking post extending from the stem and engaging with the ulna.

5. A distal radioulnar joint prosthesis as recited in claim 1, wherein said ulnar component includes a set screw, and said collar and said shell are attached to said stem by the set screw.

6. A distal radioulnar joint prosthesis as recited in claim 1, wherein said stem of said ulnar component is semi-flexible.

7. A distal radioulnar joint prosthesis as recited in claim 6, wherein said stem includes a titanium core and an outer layer of a superelastic material.

8. A distal radioulnar joint prosthesis as recited in claim 7, wherein said superelastic material is Nitinol.

9. A distal radioulnar joint prosthesis as recited in claim 7, wherein said stem is coated with hydroxyapatite.

10. A distal radioulnar joint prosthesis as recited in claim 7, wherein the outer layer of the stem comprises spiraling sheets.

11. A distal radioulnar joint prosthesis as recited in claim 10, wherein said ulnar component includes a set screw dimensioned to be received in the stem, and rotation of the set screw causes the spiraling sheets to separate.

12. A distal radioulnar joint prosthesis as recited in claim 11, wherein said spiraling sheets separate such that the separated spiraling sheets are against endosteal bone.

13. A distal radioulnar joint prosthesis as recited in claim 1, wherein said stem of said ulnar component is bowed.

14. A distal radioulnar joint prosthesis as recited in claim 1, wherein said plate of said radial component has a reverse triangular shape.

15. A distal radioulnar joint prosthesis as recited in claim 1, wherein said shell is ellipsoid.

16. A distal radioulnar joint prosthesis as recited in claim 1, wherein the hemispherical ball is connected to the plate by a rod.

17. A distal radioulnar joint prosthesis as recited in claim 16, wherein the rod has a length that is adjustable.

18. A distal radioulnar joint prosthesis as recited in claim 1, wherein the shell has a concave articulating surface including a major radius of curvature and a minor radius of curvature.

19. A distal radioulnar joint prosthesis as recited in claim 1, wherein the shell has a concave articulating surface that contacts the ball when the prosthesis is implanted in the distal radioulnar joint, the concave articulating surface being larger than the ball by a first distance in a distal-proximal plane of the distal radioulnar joint, and the concave articulating surface being larger than the ball by a second distance in a dorsal-palmar plane of the distal radioulnar joint when the prosthesis is implanted in the distal radioulnar joint.

20. A distal radioulnar joint prosthesis as recited in claim 19, wherein the second distance is greater than the first distance.

21. A distal radioulnar joint prosthesis as recited in claim 1, wherein the shell and the ball are coupled and configured to provide for translation along a distal-proximal plane of the distal radioulnar joint, and rotation around a distal-proximal plane of the distal radioulnar joint, and translation along a dorsal-palmar plane of the distal radioulnar joint when the prosthesis is implanted in the distal radioulnar joint.

22. A distal radioulnar joint prosthesis as recited in claim 21, wherein:
when the wrist supinates, the ball translates palmar, and
when the wrist pronates, the ball translates dorsal.

* * * * *